(12) United States Patent
Labit et al.

(10) Patent No.: US 8,262,635 B2
(45) Date of Patent: Sep. 11, 2012

(54) REUSABLE DIAPERS

(75) Inventors: Jennifer Lynn Labit, Arnold, MO (US); James Andrew Labit, Arnold, MO (US)

(73) Assignees: Jennifer Lynn Labit, Arnold, MO (US); James Andrew Labit, Arnold, MO (US)

( * ) Notice: Subject to any disclaimer, the term of this patent is extended or adjusted under 35 U.S.C. 154(b) by 183 days.

(21) Appl. No.: 12/059,856

(22) Filed: Mar. 31, 2008

(65) Prior Publication Data
US 2008/0183148 A1 Jul. 31, 2008

Related U.S. Application Data

(63) Continuation-in-part of application No. 11/518,587, filed on Sep. 8, 2006.

(51) Int. Cl.
*A61F 13/15* (2006.01)

(52) U.S. Cl. ......... 604/385.14; 604/385.19; 604/385.15; 604/389; 604/378; 604/385.03; 604/391; 604/392

(58) Field of Classification Search .................. 604/367, 604/370, 372, 377–378, 373, 384, 385.01, 604/385.03, 385.06, 385.14–385.15, 385.19, 604/385.23–385.3, 386, 389–402
See application file for complete search history.

(56) References Cited

U.S. PATENT DOCUMENTS

| | | | |
|---|---|---|---|
| 1,961,515 A | 6/1934 | Friedman |
| 2,016,355 A | 10/1935 | Alsop |
| 2,049,913 A | 8/1936 | Lesueur |
| RE20,315 E | 3/1937 | Lesueur |
| 2,292,030 A | 8/1942 | Kraft |
| 2,450,059 A | 9/1948 | Rickerson |
| 2,468,445 A | 4/1949 | Hurst |
| 2,493,492 A | 1/1950 | Malamut |
| 2,523,079 A | 9/1950 | Walter et al. |
| 2,532,029 A | 11/1950 | Medoff |
| 2,545,216 A | 3/1951 | Toussie |
| 2,568,590 A | 9/1951 | Laser |

(Continued)

FOREIGN PATENT DOCUMENTS

AU 5039493 1/1994

(Continued)

OTHER PUBLICATIONS

Derwent abstract and Figure of CA 2024375 A, publication date Mar. 1, 1992.*

(Continued)

*Primary Examiner* — Jacqueline F. Stephens
(74) *Attorney, Agent, or Firm* — Harness, Dickey & Pierce, P.L.C.

(57) ABSTRACT

A reusable diaper may include an inner layer and an outer layer. A fluid-absorbing insert may be coupled to the inner layer for use in absorbing fluids. The inner layer may be disposed generally between the outer layer and the fluid-absorbing insert such that both the fluid-absorbing insert and the inner layer are in position for absorbing fluids. The fluid-absorbing insert may be adjustable relative to the inner layer for accommodating use by a male and/or a female. The reusable diaper may also include forward and rearward waist portions generally defined by the inner and outer layers. Liquid-resistant regions may be disposed adjacent the waist portions, generally between the waist portions and the fluid-absorbing insert, for resisting movement of fluid from the fluid-absorbing insert to the waist portions.

24 Claims, 5 Drawing Sheets

U.S. PATENT DOCUMENTS

| | | | | |
|---|---|---|---|---|
| 2,575,164 A | | 11/1951 | Donovan | |
| 2,577,398 A | | 12/1951 | Blake | |
| 2,581,904 A | | 1/1952 | Burns | |
| 2,591,079 A | | 4/1952 | Leaton | |
| 2,607,348 A | | 8/1952 | Rosenblatt | |
| 2,627,859 A | | 2/1953 | Hargrave | |
| 2,664,895 A | | 1/1954 | Shulman | |
| 2,688,328 A | | 9/1954 | Marcus | |
| 2,703,577 A | | 3/1955 | May | |
| 2,733,715 A | * | 2/1956 | Folk | 604/398 |
| 2,788,786 A | | 4/1957 | Dexter | |
| 2,826,199 A | | 3/1958 | Brandon | |
| 2,853,073 A | | 9/1958 | Brafman | |
| 2,866,459 A | | 12/1958 | Sobelson | |
| 2,868,205 A | | 1/1959 | Epstein | |
| 2,893,393 A | | 7/1959 | Pressley | |
| 2,910,982 A | | 11/1959 | Woodward | |
| 2,985,170 A | | 5/1961 | Title | |
| 3,049,124 A | * | 8/1962 | Thompson | 604/399 |
| 3,141,461 A | | 7/1964 | Farris | |
| 3,162,196 A | * | 12/1964 | Salk | 604/399 |
| 3,341,394 A | | 9/1967 | George | |
| 3,485,706 A | | 12/1969 | Franklin | |
| 3,530,859 A | | 9/1970 | Helmowitz | |
| 3,559,648 A | * | 2/1971 | Mason, Jr. | 604/375 |
| 3,658,064 A | | 4/1972 | Pociluyko | |
| 3,667,466 A | | 6/1972 | Ralph | |
| 3,741,212 A | | 6/1973 | Schutte | |
| 3,769,978 A | | 11/1973 | DeNight et al. | |
| 3,882,871 A | | 5/1975 | Taniguchi | |
| RE28,483 E | | 7/1975 | Ralph | |
| 3,926,189 A | * | 12/1975 | Taylor | 604/359 |
| 4,037,602 A | * | 7/1977 | Hawthorne | 604/375 |
| 4,338,939 A | | 7/1982 | Daville | |
| D269,907 S | | 7/1983 | Tong | |
| 4,414,971 A | | 11/1983 | Chung et al. | |
| 4,548,604 A | | 10/1985 | Ellsworth | |
| 4,568,342 A | | 2/1986 | Davis | |
| 4,573,987 A | | 3/1986 | Lamb, Jr. | |
| 4,643,726 A | | 2/1987 | Gegelys | |
| 4,671,793 A | | 6/1987 | Hults et al. | |
| 4,681,581 A | | 7/1987 | Coates | |
| 4,695,279 A | | 9/1987 | Steer et al. | |
| 4,704,117 A | * | 11/1987 | Mitchell | 604/391 |
| 4,773,906 A | * | 9/1988 | Krushel | 604/391 |
| 4,834,737 A | | 5/1989 | Khan | |
| 4,850,987 A | | 7/1989 | Gilomen et al. | |
| 4,892,598 A | | 1/1990 | Stevens et al. | |
| 4,904,251 A | | 2/1990 | Igaue et al. | |
| 4,906,243 A | | 3/1990 | Dravland | |
| 4,928,323 A | | 5/1990 | Nathan | |
| 4,950,263 A | * | 8/1990 | Lewis | 604/385.01 |
| 4,961,736 A | | 10/1990 | McCloud | |
| 4,981,480 A | | 1/1991 | Gaudet et al. | |
| 5,019,068 A | | 5/1991 | Perez et al. | |
| 5,069,672 A | | 12/1991 | Wippler et al. | |
| 5,100,399 A | | 3/1992 | Janson et al. | |
| 5,106,382 A | * | 4/1992 | Henry | 604/385.15 |
| 5,108,385 A | | 4/1992 | Snyder | |
| 5,135,522 A | | 8/1992 | Fahrenkrug et al. | |
| 5,137,526 A | | 8/1992 | Coates | |
| 5,185,011 A | | 2/1993 | Strasser | |
| 5,207,662 A | | 5/1993 | James | |
| 5,217,447 A | * | 6/1993 | Gagnon | 604/397 |
| D339,633 S | | 9/1993 | Porter | |
| 5,306,267 A | * | 4/1994 | Hahn et al. | 604/378 |
| 5,325,543 A | | 7/1994 | Allen | |
| 5,342,340 A | * | 8/1994 | Kichefski et al. | 604/385.25 |
| 5,360,422 A | | 11/1994 | Brownlee et al. | |
| D354,809 S | | 1/1995 | Eskey | |
| 5,399,177 A | | 3/1995 | Blaney et al. | |
| 5,405,342 A | | 4/1995 | Roessler et al. | |
| 5,409,476 A | | 4/1995 | Coates | |
| D362,717 S | | 9/1995 | Caschette et al. | |
| 5,454,799 A | | 10/1995 | Lakiss-Smith et al. | |
| 5,458,591 A | | 10/1995 | Roessler et al. | |
| 5,476,457 A | | 12/1995 | Roessler et al. | |
| D366,112 S | | 1/1996 | Tollin et al. | |
| 5,514,121 A | | 5/1996 | Roe et al. | |
| 5,527,300 A | | 6/1996 | Sauer | |
| 5,611,789 A | | 3/1997 | Seth | |
| 5,613,959 A | | 3/1997 | Roessler et al. | |
| D386,582 S | | 11/1997 | Levine | |
| 5,695,488 A | | 12/1997 | Sosalla | |
| 5,706,524 A | | 1/1998 | Herrin et al. | |
| 5,722,127 A | | 3/1998 | Coates | |
| 5,725,518 A | | 3/1998 | Coates | |
| 5,814,037 A | | 9/1998 | Coates | |
| 5,891,122 A | | 4/1999 | Coates | |
| D436,400 S | | 1/2001 | Kiecker | |
| 6,168,583 B1 | | 1/2001 | Tanji et al. | |
| 6,254,583 B1 | | 7/2001 | Coates | |
| 6,315,764 B1 | | 11/2001 | Faulks et al. | |
| 6,322,552 B1 | | 11/2001 | Blenke et al. | |
| 6,379,343 B2 | | 4/2002 | Stephenson et al. | |
| 6,383,170 B1 | | 5/2002 | Mishima et al. | |
| 6,402,731 B1 | | 6/2002 | Suprise et al. | |
| 6,423,047 B1 | | 7/2002 | Webster | |
| 6,471,681 B1 | | 10/2002 | Rönnberg et al. | |
| 6,482,194 B1 | | 11/2002 | Putzer | |
| 6,540,730 B1 | | 4/2003 | Niedermeyer | |
| 6,562,016 B2 | * | 5/2003 | Shinkai | 604/385.01 |
| 6,569,137 B2 | | 5/2003 | Suzuki et al. | |
| 6,579,273 B2 | | 6/2003 | Dupuy | |
| 6,616,645 B1 | | 9/2003 | Moravek | |
| 6,623,466 B1 | | 9/2003 | Richardson | |
| 6,641,569 B1 | | 11/2003 | Coles et al. | |
| 6,766,817 B2 | | 7/2004 | da Silva et al. | |
| 6,767,498 B1 | | 7/2004 | Talley et al. | |
| 6,918,404 B2 | | 7/2005 | da Silva et al. | |
| 6,989,005 B1 | | 1/2006 | LaVon et al. | |
| 7,066,586 B2 | | 6/2006 | da Silva et al. | |
| 7,244,398 B2 | | 7/2007 | Kotary et al. | |
| 7,285,255 B2 | | 10/2007 | Kadlec et al. | |
| 7,361,803 B2 | | 4/2008 | Miskie | |
| 7,591,811 B2 | | 9/2009 | Wilkinson | |
| 7,629,501 B2 | | 12/2009 | Labit et al. | |
| 2002/0010452 A1 | | 1/2002 | Dupuy | |
| 2002/0094740 A1 | | 7/2002 | Li et al. | |
| 2003/0014024 A1 | | 1/2003 | Kiecker | |
| 2003/0083635 A1 | | 5/2003 | Gibbs | |
| 2003/0109841 A1 | | 6/2003 | Edwards | |
| 2004/0044323 A1 | | 3/2004 | Roessler et al. | |
| 2004/0082933 A1 | | 4/2004 | Karami | |
| 2004/0236298 A1 | | 11/2004 | Coates | |
| 2004/0236300 A1 | | 11/2004 | Gibbs et al. | |
| 2004/0267219 A1 | | 12/2004 | Olmedo | |
| 2005/0085784 A1 | * | 4/2005 | LeMinh et al. | 604/387 |
| 2005/0148258 A1 | | 7/2005 | Chakravarty et al. | |
| 2005/0210560 A1 | | 9/2005 | Coates | |
| 2005/0228356 A1 | | 10/2005 | LaVon et al. | |
| 2006/0167432 A1 | | 7/2006 | Sigari | |
| 2007/0066952 A1 | | 3/2007 | LaVon et al. | |
| 2008/0015531 A1 | | 1/2008 | Hird et al. | |
| 2008/0065039 A1 | | 3/2008 | Labit et al. | |
| 2008/0215027 A1 | | 9/2008 | Labit et al. | |
| 2010/0036340 A1 | | 2/2010 | Allison-Rogers | |
| 2010/0087794 A1 | | 4/2010 | Labit et al. | |
| 2010/0108554 A1 | | 5/2010 | Melius et al. | |
| 2011/0137278 A1 | | 6/2011 | Ormsby et al. | |

FOREIGN PATENT DOCUMENTS

| | | | |
|---|---|---|---|
| BR | 03606/71 | | 12/1971 |
| BR | 360571 | | 12/1971 |
| CA | 2097437 | | 12/1993 |
| CA | 2103537 A | * | 2/1995 |
| DE | 4326271 | | 2/1995 |
| EP | 0099846 | | 2/1984 |
| EP | 0486006 | | 11/1991 |
| EP | 0475702 | | 3/1992 |
| ES | 2115559 | | 6/1998 |
| GB | 493819 | | 10/1938 |
| GB | 0849573 | | 9/1960 |
| GB | 0803716.0 | | 2/2008 |
| JP | 04150853 | | 5/1992 |
| JP | 08000662 | | 1/1996 |
| WO | WO-8705471 | | 9/1987 |

| | | |
|---|---|---|
| WO | WO-9007313 | 7/1990 |
| WO | WO-9403137 | 2/1994 |
| WO | WO-94/15563 A1 | 7/1994 |
| WO | WO-95/23569 | 9/1995 |
| WO | WO-9824388 | 6/1998 |
| WO | WO 9933421 A1 * | 7/1999 |
| WO | WO-2008030984 | 3/2008 |
| WO | WO-2008/142634 | 11/2008 |
| WO | WO 2009/106899 | 9/2009 |
| ZA | 8701842 | 11/1988 |

OTHER PUBLICATIONS

Definition of "waterproof", Webster's Third New International Dictionary, unabridged, 1993.* http://www.wonderworksbabyco.com/products.htm, 5 pages, accessed and printed Sep. 8, 2006.

http://fuzzibunz.com/Fuzzi-Bunz-Colors.htm, 2 pages, accessed and printed Sep. 8, 2006.

http://www.tinytush.com/6 pages, accessed and printed Sep. 8, 2006.

http://web.archive.org/web/20041010045134/www.changingbabies.com/anatomyofadiaper.html; accessed Apr. 27, 2007, 17 pages.

http://www.aplix.com/en/layout/set/print/content/search, accessed Apr. 27, 2007, 3 pages.

http://www.cottonbabies.com/index.php, 7 pages, accessed on Aug. 24, 2006.

http://www.diapersite.com/baby_diapers_specs.htm, 4 pages, accessed Apr. 23, 2008.

http://www.diapersite.com/images/diaperspecs/velcro.htm, 1 page, accessed Apr. 23, 2008.

http://tubarc.blogspot.com/, 206 pages, accessed Sep. 15, 2008.

http://hydrology-tubarc.blogspot.com/ 32 pages, accessed Sep. 15, 2008.

http://ip-know-how-tubarc.blogspot.com/, 8 pages, accessed Sep. 15, 2008.

Derwent Abstract and Figure of AU 9539089 A, published Jun. 27, 1996.

FuzziBunz, A better diaper for a better planet, Newsletter, FuzziBunz Press Releases, 5 pages, (Jul. 10, 2007).

* cited by examiner

REUSABLE DIAPERS

CROSS-REFERENCE TO RELATED APPLICATION

This application is a continuation-in-part of U.S. patent application Ser. No. 11/518,587 filed Sep. 8, 2006, the entire disclosure of which is incorporated herein by reference.

FIELD

The present disclosure relates generally to reusable diapers.

BACKGROUND

The statements in this background section merely provide background information related to the present disclosure and may not constitute prior art.

Absorbent articles, such as disposable diapers, training pants, or incontinence pads, generally have an absorbent core intended for single use only. Once the absorbent core component is saturated with bodily discharges, such as urine, the entire absorbent article is usually discarded. Oftentimes, parts of a disposable diaper or training pants could be reused. But with the unitary construction, they are nevertheless discarded along with the saturated absorbent cores. In addition to the added cost and waste associated with discarding such products, it is often inconvenient to acquire and store quantities of such disposable absorbent articles.

SUMMARY

According to various aspects, exemplary embodiments are provided of reusable diapers. In one exemplary embodiment, a gender neutral reusable diaper generally includes at least one inner layer and at least one outer layer. At least one fluid-absorbing insert is coupled to the inner layer for use in absorbing fluids. The at least one inner layer is disposed generally between the at least one outer layer and the at least one fluid-absorbing insert. The at least one fluid-absorbing insert is adjustable relative to the at least one inner layer for accommodating use by a male and/or a female.

In another exemplary embodiment, a gender neutral reusable diaper generally includes a waist portion, at least one fluid-absorbing insert for use in absorbing fluids, and at least one liquid-resistant region disposed adjacent the waist portion between the waist portion and the at least one fluid-absorbing insert for resisting movement of fluid from the at least one fluid-absorbing insert to the waist portion. The at least one fluid-absorbing insert is adjustable relative to the waist portion by folding at least part of the at least one fluid-absorbing insert over itself at a desired location within the reusable diaper for accommodating use of the reusable diaper by a male and/or a female.

In another exemplary embodiment, a reusable diaper generally includes at least one inner layer, at least one outer layer, a forward waist portion, and a rearward waist portion. The at least one inner layer includes at least one forward liquid-resistant region disposed adjacent the forward waist portion for resisting movement of moisture through the at least one inner layer past the at least one forward liquid-resistant region. The at least one inner layer also includes at least one rearward liquid-resistant region disposed adjacent the rearward waist portion for resisting movement of moisture through the at least one inner layer past the at least one rearward liquid-resistant region.

Further aspects and features of the present disclosure will become apparent from the detailed description provided hereinafter. In addition, any one or more aspects of the present disclosure may be implemented individually or in any combination with any one or more of the other aspects of the present disclosure. It should be understood that the detailed description and specific examples, while indicating exemplary embodiments of the present disclosure, are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
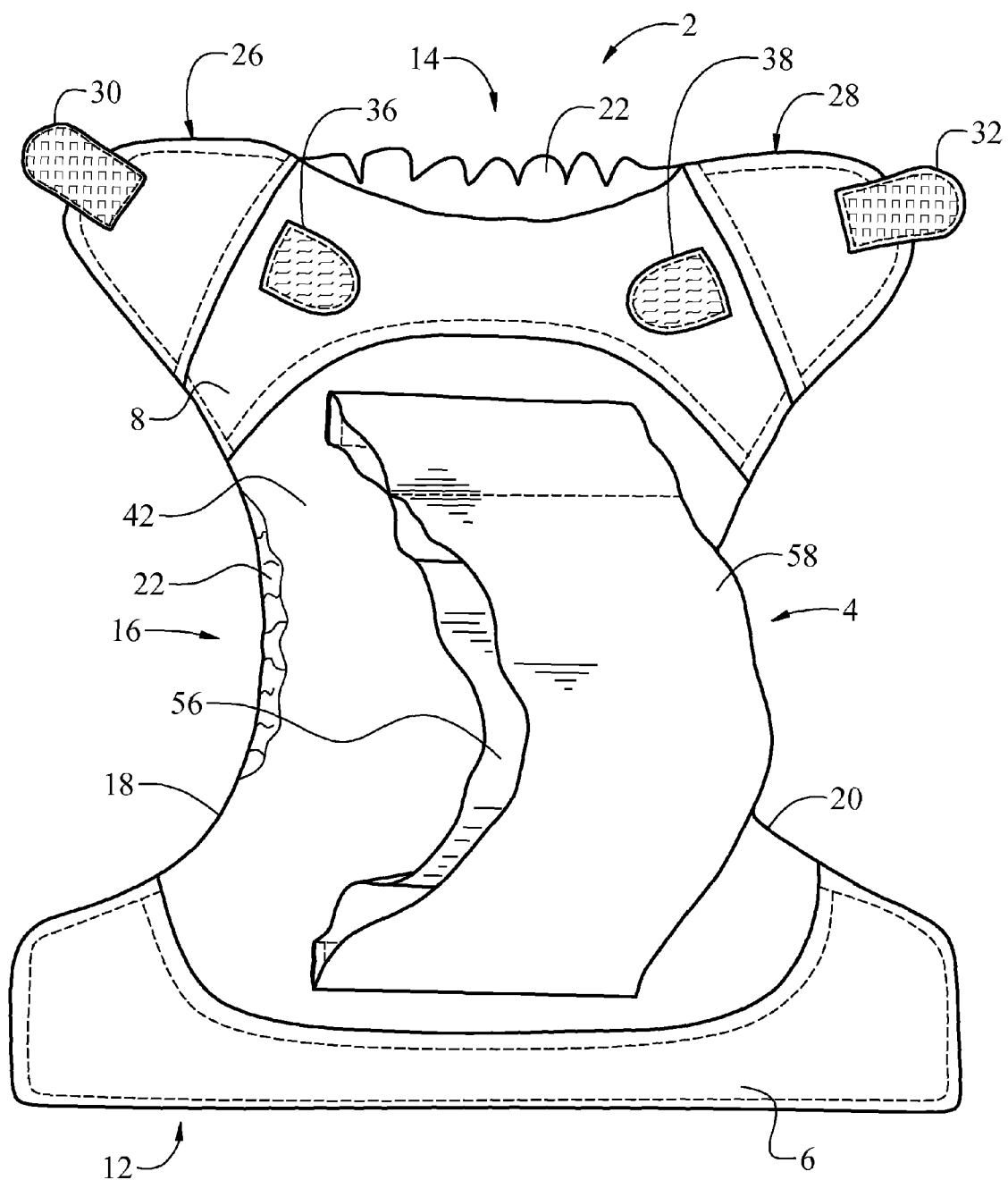
FIG. 1 is an inner perspective view of an exemplary embodiment of a gender neutral reusable diaper having an adjustable fluid-absorbing insert for use in absorbing fluids within the reusable diaper.

The following description is merely exemplary in nature and is not intended to limit the present disclosure, application, or uses. It should be understood that throughout the drawings, corresponding reference numerals indicate like or corresponding parts and features.

Referring now to the drawings, FIGS. 1-5 illustrate an exemplary embodiment of an adjustable, gender neutral reusable diaper 2 embodying one or more aspects of the present disclosure. As will be described, the exemplary reusable diaper 2 may be adjusted as desired to accommodate use by a male and/or a female wearer. More particularly, a fluid-absorbing insert 4 of the reusable diaper 2 may be adjusted as desired to accommodate use by the male and/or female wearer. As will also be described, the reusable diaper 2 may also be adjusted (e.g., via adjustment system 46, etc.) to fit different sized male and/or female wearers, and/or may include liquid-resistant regions 6, 8 located to help resist undesired movement of moisture through the reusable diaper 2 (e.g., through forward and rearward waist portions 12, 14, etc.).

Figure 2:
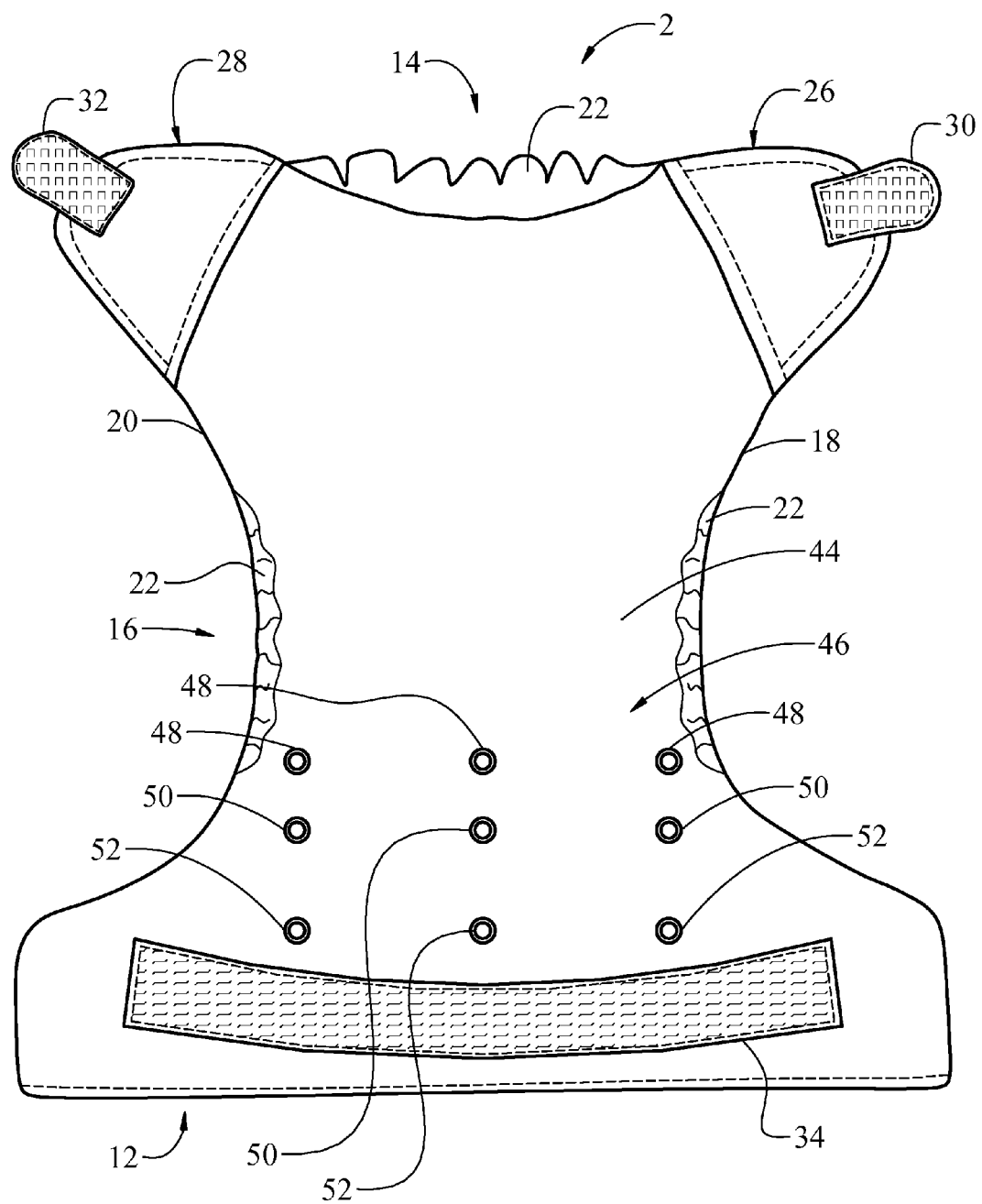
FIG. 2 is an outer view of the reusable diaper shown in FIG. 1.
Figure 3:
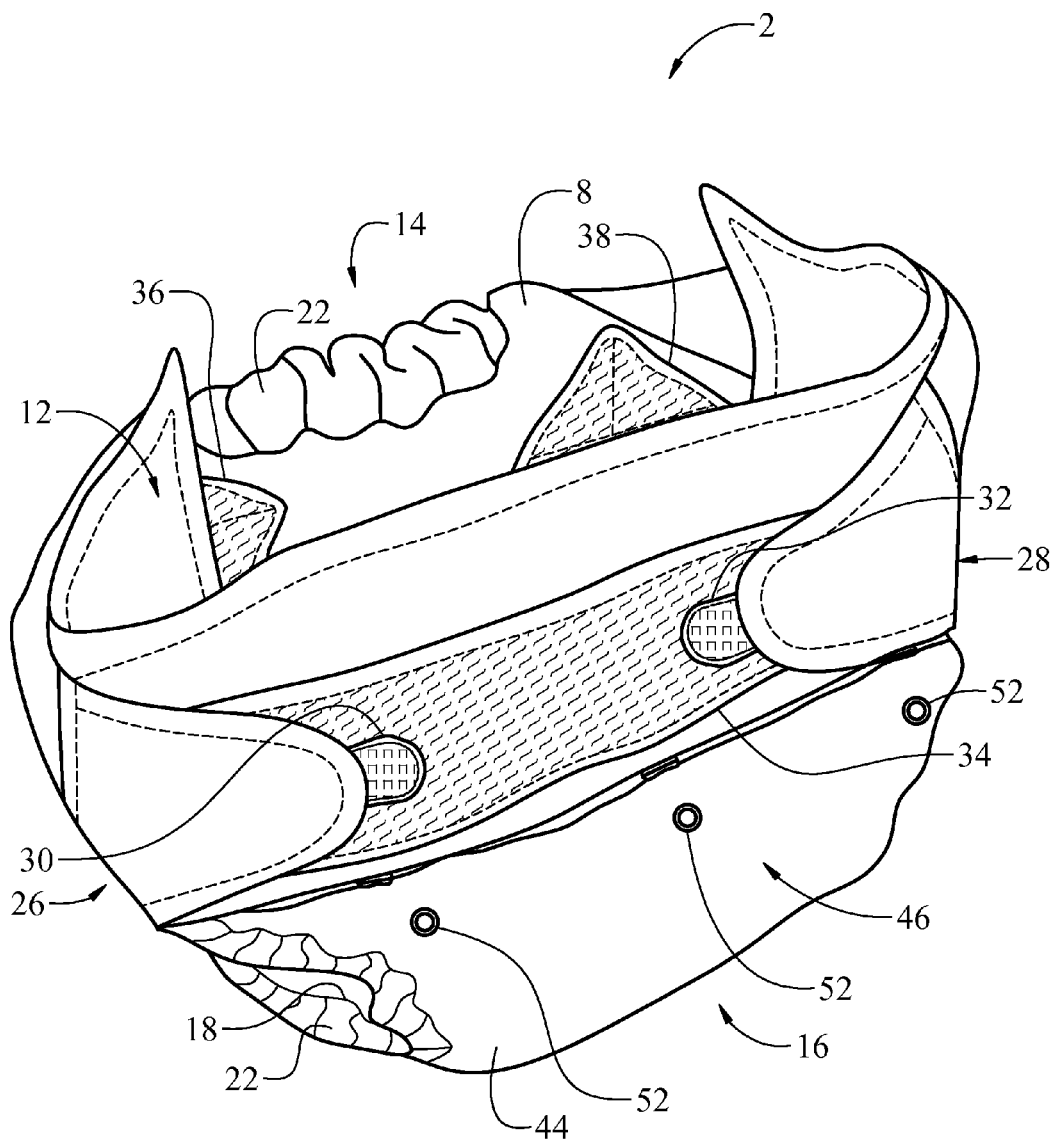
FIG. 3 is a perspective view of the reusable diaper of FIG. 1 shown secured in a generally closed position.

With reference to FIGS. 1-3, the reusable diaper 2 generally includes a forward waist portion 12, a rearward waist portion 14, and a crotch portion 16 disposed generally between the forward and rearward waist portions 12, 14. The contours of the forward and rearward waist portions 12, 14, together with the crotch portion 16, cooperatively define leg openings 18, 20 generally within the crotch portion 16 to accommodate a wearer's legs. In the illustrated embodiment, the leg openings 18, 20 include elastic 22 disposed adjacent the periphery of the leg openings 18, 20 for example, to help draw and hold the reusable diaper 2 securely against the wearer's legs, to inhibit leaking of fluids out of the reusable diaper 2 through the leg openings 18, 20, etc.

The rearward waist portion 14 of the reusable diaper 2 includes corner regions 26, 28 that may be releasably attached to the forward waist portion 12 to secure the reusable diaper 2 in a desired position (e.g., in a generally closed position as shown in FIG. 3, etc.). More particularly, tabs 30, 32 of the respective corner regions 26, 28 may be releasably attached (e.g., via corresponding hook-and-loop fasteners, etc.) to an elongate strip 34 of the forward waist portion 12 to secure the diaper 2 in the desired position (e.g., in the generally closed position, etc.). Elastic 22 is disposed along the rearward waist portion 14 to help ensure a snug fit of the reusable diaper 2 around a wearer's waist.

The tabs 30, 32 of the reusable diaper's corner regions 26, 28 may also be releasably attached to each other, for example, for closing the diaper 2 for storage, etc. For example, one of the tabs 30, 32 may have a forward surface with hook-and-loop fasteners that are releasably attachable to corresponding hook-and-look fasteners on a rearward surface of the other tab 30, 32. The tabs 30, 32 may also be releasably attached to interior laundry closures 36, 38 of the rearward waist portion 14 (e.g., via corresponding hook-and-loop fasteners, etc.). This may, for example, help prevent or at least reduce snagging of the tabs 30, 32 when the reusable diaper 2 is being washed or laundered.

The corner regions 26, 28 and/or the tabs 30, 32 of the reusable diaper 2 may also be resiliently stretchable. This may allow for at least some adjustability of the diaper's functional waist size as defined by the forward and rearward waist portions 12, 14 when the rearward waist portion 14 is releasably attached to the forward waist portion 12 (e.g., via tabs 30, 32, etc.) in the generally closed position. For example, the corner regions 26, 28 may be formed from about 95% polyester and about 5% Lycra to allow them to stretch. However, the corner regions 26, 28 may be formed from other suitable materials within the scope of the present disclosure, and may or may not be resiliently stretchable.

Having resiliently elastic or stretchable corner regions 26, 28 (and/or tabs 30, 32 and/or elastic 22) with the ability to stretch can allow for tailoring of the diaper's functional waist size to the wearer's actual waist size. For example, the diaper's functional waist size may be selectively tailored for the wearer by stretching the corner regions 26, 28 (and/or tabs 30, 32 and or elastic 22), and then releasably attaching the tabs 30, 32 to the elongate strip 34 at desired attachment locations along the length of the elongate strip 34. In this exemplary manner, the diaper's functional waist size can be selectively adjusted, for example, to provide a relatively snug fit about the waist of the wearer (e.g., infant, toddler, adult, etc.), and preferably without being too uncomfortably tight about the wearer's thighs.

While the tabs 30, 32, the elongate strip 34, and the laundry closures 36, 38 of the reusable diaper 2 are each disclosed as including corresponding hook-and-loop fasteners, other suitable fasteners for coupling corresponding portions of the reusable diaper 2 together may be used within the scope of the present disclosure. For example, tabs, elongate strips, and/or laundry closures may include one or more of different hook-and-loop fastener arrangements (e.g., two or more spaced-apart discrete patches along the second waist portion instead of a single elongate strip, etc.), adhesives, snaps, buttons, clasps, various hook and loop closures, magnets, combinations thereof, etc. within the scope of the present disclosure.

With continued reference to FIGS. 1-3, the illustrated reusable diaper 2 also generally includes an inner layer 42 (FIGS. 1 and 3) and an outer layer 44 (FIGS. 2 and 3) generally coupled to the inner layer 42 (e.g., seamed, stitched, melted, etc.). The inner layer 42 and the outer layer 44 may broadly be viewed as defining at least part of the forward and rearward waist portions 12, 14, and at least part of the crotch portion 16 of the reusable diaper 2. The inner layer 42 may be configured to absorb, wick, etc. moisture generally away, for example, from a diaper wearer, and may be formed of, for example, organic cotton, any suitable absorbent material, etc. The outer layer 44 may be configured to be substantially liquid-impervious to thereby resist wicking of moisture through the outer layer 44, and may be formed of polyester, water resistant material, coated materials, laminated materials, etc.

With particular reference to FIG. 1, the inner layer 42 includes two liquid-resistant regions 6, 8 that, for example, help resist wicking, movement, etc. of moisture through the inner layer 42 past the liquid-resistant regions 6, 8. A forward liquid-resistant region 6 is disposed adjacent the forward waist portion 12, and a rearward liquid-resistant region 8 is disposed adjacent the rearward waist portion 12, 14. The forward and rearward liquid-resistant regions 6, 8 each generally include a strip of material that may be coupled (e.g., seamed, stitched, melted, etc.), for example, to the inner layer 42 and/or to the outer layer 44. Each liquid-resistant region 6, 8 extends generally across a width of the reusable diaper's inner layer 42 to resist wicking, movement, etc. of moisture substantially along the width of the inner layer 42. As such, the forward liquid-resistant region 6 may be viewed as defining at least part of the forward waist portion 12, and the rearward liquid-resistant region 8 may be viewed as defining at least part of the rearward waist portion 14. It should be appreciated that a wide range of suitable materials, coatings, etc. may be used for the liquid-resistant regions 6, 8, including, for example, polyester materials, durable water repellant coatings, laminated fabrics, coated fabrics, etc.

As stated above, the two liquid-resistant regions 6, 8 of the illustrated reusable diaper 2 may help resist wicking, movement, etc. of moisture through the diaper 2 past the liquid-resistant regions 6, 8. In the illustrated embodiment, for example, the forward and rearward liquid-resistant regions 6, 8 are generally disposed adjacent the respective forward and rearward waist portions 12, 14, generally between the waist portions 12, 14 and the fluid-absorbing insert 4. This positioning may help resist wicking, movement, etc. of fluid from the fluid-absorbing insert 4, the inner layer 42, etc., through the forward and/or rearward waist portions 12 and/or 14 and to a shirt, blanket, article of bedding, etc. that may come into contact with the respective forward and/or rearward waist portions 12 and/or 14 (e.g., with an inner part of the forward and/or rearward waist portions 12 and/or 14, etc.). In other exemplary embodiments, reusable diapers may include inner layers having liquid-resistant regions shaped differently than disclosed herein; having liquid-resistant regions disposed, located, etc. differently than disclosed herein; having liquid-resistant regions with one or more separated parts; having less than or more than two liquid-resistant regions; etc. For example, in one exemplary embodiment, one or more liquid-resistant regions may be disposed adjacent one or more of a forward waist portion, a rearward waist portion, leg regions, etc. of a reusable diaper.

With particular reference now to FIGS. 2 and 3, an adjustment system 46 is provided along the outer layer 44 of the reusable diaper adjacent the forward waist portion 12 to allow for customization or adjustment to the reusable diaper's functional rise and/or crotch length. For example, the adjustment system 46 may allow for adjustment of the reusable diaper 2 such that the reusable diaper 2 may be adjusted to fit different sized wearers. This feature, in combination with the resiliently elastic or stretchable corner regions 26, 28 (and/or tabs 30, 32), elastic 22, etc.), may provide a generally one-size-fits all reusable diaper 2. This feature may also help create an even better and/or snugger fit to the diaper wearer (e.g., in combination with the resiliently elastic or stretchable corner regions 26, 28 (and/or tabs 30, 32), elastic 22, etc.). For example, the adjustment system 46 may help reduce the extent to which the crotch portion 16 hangs down below the wearer, and the corner region 26, 28 (and/or tabs 30, 32) and/or elastic 22 may help securely hold the reusable diaper 2 around a wearer's waist and/or legs. Adjustment systems may be located differently than disclosed herein (e.g., adjacent rearward waist portions, adjacent crotch portions, etc.) within the scope of the present disclosure.

The illustrated adjustment system 46 includes a three-by-three array of snaps 48, 50, 52, horizontally arranged and aligned in three rows and vertically arranged and aligned in three columns. A first row includes three spaced-apart male snaps 48; a second, or middle, row includes three spaced-apart female snaps 50; and a third row includes three-spaced apart female snaps 52. The male snaps 48 can be snapped together with either the female snaps 50 of the second row, or the female snaps 52 of the third row. For example, as shown in FIG. 3, the male snaps 48 of the first row can be snapped together with the corresponding female snaps 50 of the second row to thereby decrease the diaper's functional rise and/or crotch length. To decrease the diaper's functional rise and/or crotch length to an even greater extent, the male snaps 48 of the first row may instead be snapped together with the corresponding female snaps 52 of the third row.

The illustrated array of snaps 48, 50, 52 thus provide three different sizing configurations for the reusable diaper 2. The functional rise and/or crotch length of the reusable diaper 2 may be changed by selectively choosing whether to engage the male snaps 48 with the female snaps 50 of the second row, with the female snaps 52 of the third row, or by simply choosing to do neither. Thus, the exemplary three-by-three arrangement can eliminate or at least reduce the bulge in the middle front of the diaper 2 that typically occurs when there are only two columns of snaps due to the fabric bulging out between the two snaps. The three-by-three snap arrangement may help enable the diaper 2 to be more of a one-size fits all diaper 2.

The snaps 48, 50, 52 of the illustrated adjustment system 46 may be formed from a plastic material. Alternatively, the snaps 48, 50, 52 may be formed from other materials, for example lightweight and durable materials that can withstand repeated laundry cycles. In other exemplary embodiments, reusable diapers may include more or less than nine snaps and/or snaps arranged differently than illustrated herein. In addition, reusable diapers may include snaps in other arrangements than disclosed herein, for example, two rows of male snaps with only one row of female snaps, or rows having both male and female snaps. Additional exemplary embodiments include reusable diapers with more or less than three rows of snap members and/or more or less than three columns of snap members.

While the illustrated adjustment system 46 includes an array of snaps 48, 50, 52, other exemplary adjustment systems may be used within the scope of the present disclosure. For example, adjustment systems may include adhesives, buttons, clasps, various hook and loop closures, magnets, elastic straps, adjustable straps, combinations thereof, etc.

Figure 4:
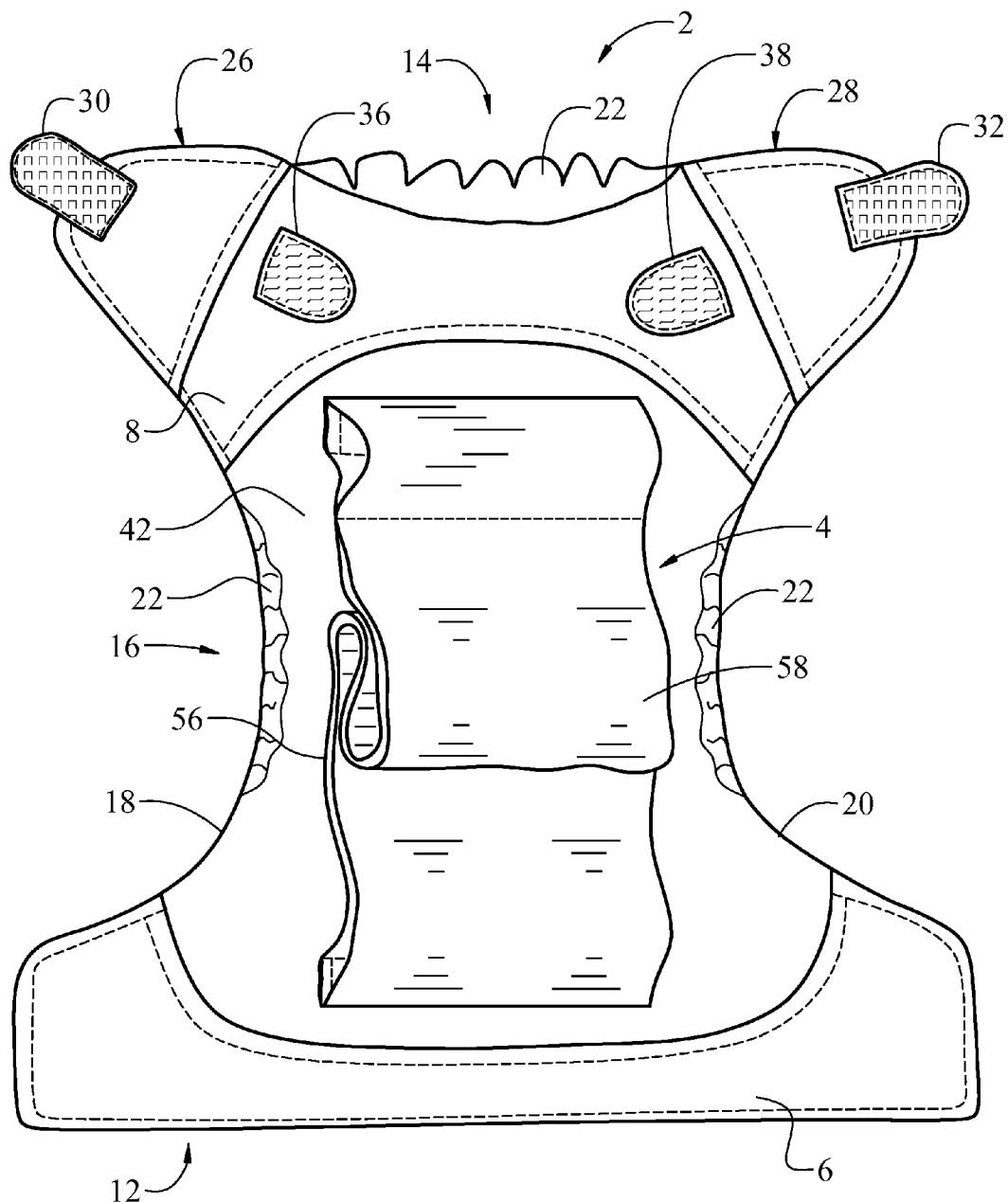
FIG. 4 is a view similar to FIG. 1 with the fluid-absorbing insert shown at least partly folded over itself in position for accommodating use by a female wearer.
Figure 5:
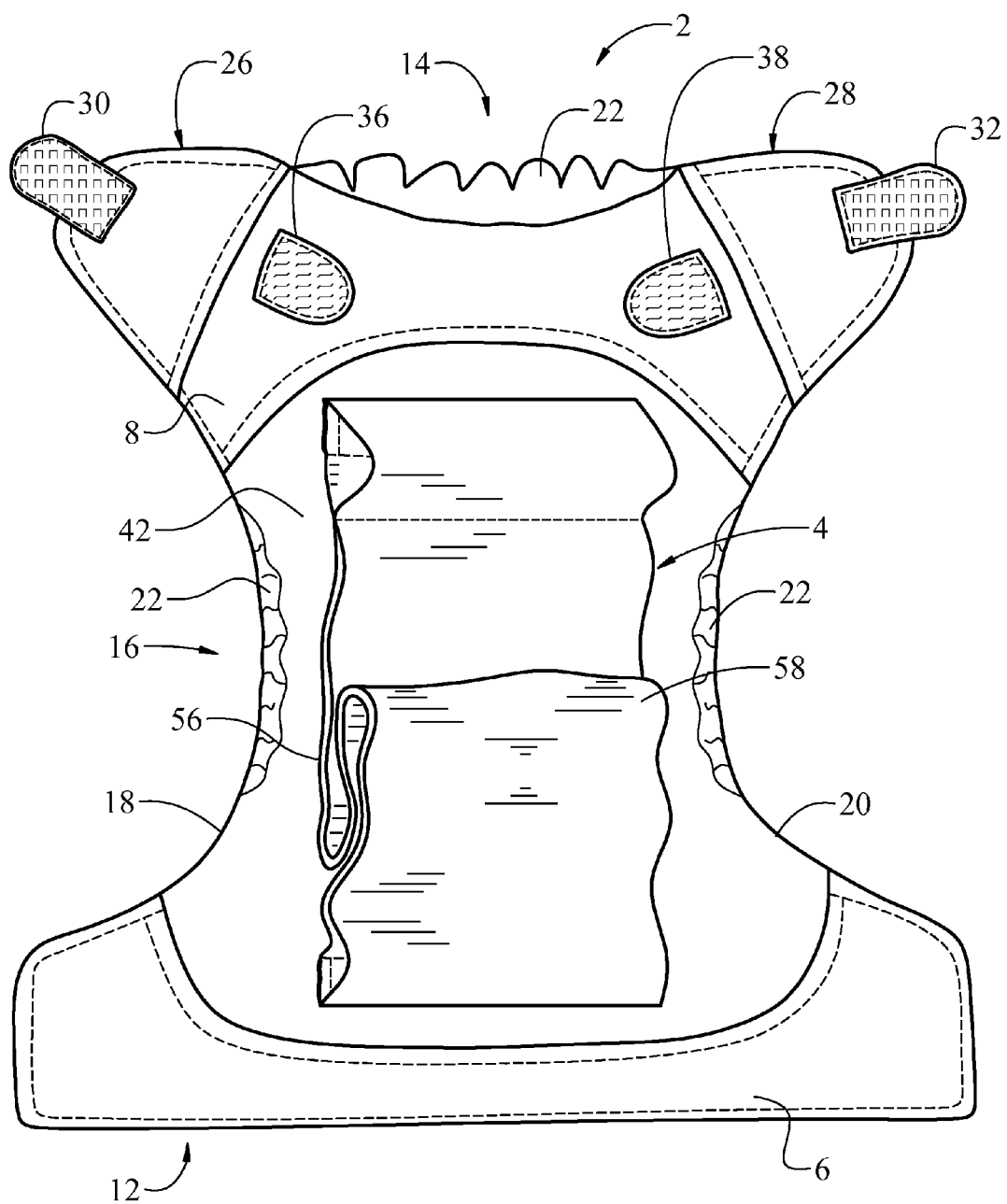
FIG. 5 is a view similar to FIG. 1 with the fluid-absorbing insert shown at least partly folded over itself in position for accommodating use by a male wearer.

With reference now to FIGS. 1, 4, and 5, the adjustable fluid-absorbing insert 4 of the reusable diaper 2 will be described. The fluid-absorbing insert 4 is positioned within the reusable diaper 2 to absorb liquids within the reusable diaper 2, for example liquids discharged into the reusable diaper 2 by a wearer, etc. In the illustrated embodiment, the fluid-absorbing insert 4 is coupled to the reusable diaper's inner layer 42 such that the inner layer 42 is disposed generally between the outer layer 44 and the fluid-absorbing insert 4. In this position, the fluid-absorbing insert 4 may absorb liquids within the reusable diaper 2 (e.g., fluids discharged by the diaper's wearer), and the inner layer 42 may absorb liquids within the reusable diaper 2 that, for example, move outwardly past the fluid-absorbing insert 4, soak through the fluid-absorbing insert 4, etc.

As best shown in FIG. 1, the illustrated fluid-absorbing insert 4 includes two individual and separate (and at least partly spaced apart) layers 56, 58 of material. The two layers 56, 58 are each stitched to the reusable diaper's inner layer 42 at two locations: a first location adjacent the forward waist portion 12 and a second location adjacent the rearward waist portion 14. For example, free ends of each of the layers 56, 58 may be overlapped and then stitched to the inner layer 42. The two layers 56, 58 may further be stitched together at a third location adjacent the rearward waist portion 14. This may help hold the two layers 56, 58 in position together, and/or may help with sizing and positioning the two layers 56, 58 as desired. In other exemplary embodiments, reusable diapers may include fluid-absorbing inserts having more than or less than two layers of material. In addition, fluid-absorbing insert layers may be coupled together differently and/or may be coupled to reusable diapers differently (e.g., to inner layers of the reusable diapers at locations other than disclosed herein (e.g., adjacent crotch portions, etc.)) within the scope of the present disclosure. Moreover, a single piece of material may be used to form fluid-absorbing insert layers.

The layers 56, 58 of the illustrated fluid-absorbing insert 4 are formed from organic cotton material. However, the fluid absorbing insert layers 56, 58 may comprise in part or in whole one or more of microfibers, hemp, hydrocolloid materials, other suitable absorbent materials, combinations thereof, etc. within the scope of the present disclosure. Materials other than organic materials may also be used.

As shown in FIGS. 4 and 5, the layers 56, 58 of the fluid-absorbing insert 4 are together adjustable relative to the reusable diaper's inner layer 42, for example, for accommodating use of the reusable diaper 2 either by a female wearer (e.g., FIG. 4, etc.) or a male wearer (e.g., FIG. 5, etc.). The fluid-absorbing insert layers 56, 58 are thus also viewed as adjustable relative to the reusable diaper's forward waist portion 12 and rearward waist portion 14, at locations generally between the forward waist portion 12 and rearward waist portion 14. Such adjustability may allow for positioning the layers 56, 58 of the fluid-absorbing insert 4 as desired to ensure that fluids, for example fluids discharged into the reusable diaper 2 by a wearer, are substantially absorbed by the fluid-absorbing insert 4. Thus, this may help inhibit fluids from pooling and/or leaking out of the reusable diaper 2 onto the wearer's clothes, body, bedding, toys, furniture, etc.

To adjust the fluid-absorbing insert 4, the layers 56, 58 are folded, bulked up, gathered, etc. over themselves to provide an overlapped, layered, built up, etc. region at the desired location (e.g., at the desired location to accommodate the female or male wearer, etc.). This overlapped region may provide additional liquid absorbing capacity (e.g., additional absorbing material, layers, etc.) at the desired location within the reusable diaper 2, and thus help inhibit undesired leaks. As shown in FIG. 4, for example, the fluid-absorbing insert layers 56, 58 can be folded over themselves adjacent the reusable diaper's crotch portion 16 to accommodate use by a female wearer. Here, the fluid-absorbing insert layers are overlapped at a typical central location to absorb fluids discharged by the female wearer. And as shown in FIG. 5, for example, the fluid-absorbing insert layers 56, 58 can be folded over themselves adjacent the reusable diaper's forward waist portion 12 to accommodate use by a male wearer. Here, the fluid-absorbing insert layers 56, 58 are overlapped at a typical forward location to absorb fluids discharged by the male wearer.

It should now be appreciated that the reusable diaper 2 may be put on either male or female wearers having varying, differing, etc. body sizes, waist sizes, etc. The adjustment system may first be adjusted to accommodate the body size of the wearer. The reusable diaper may then be put on the wearer with the fluid-absorbing insert 4 (as well as part of the inner layer 42) positioned against the skin of the wearer. The fluid-absorbing insert 4 may be folded, bulked up, etc. at the desired location to accommodate a male or female wearer. The first and second corner regions 26, 28 (e.g., the tabs 30, 32) of the rearward waist portion 14 may next be secured to the elongate strip 3 of the forward waist-portion 12 to secure the reusable diaper 2 on the wearer. In this position, the fluid-absorbing insert 4 and/or the inner layer 42 can absorb moisture from the wearer (e.g., bodily discharge, urine, sweat, etc.). When the fluid-absorbing insert 4 becomes saturated, the reusable diaper 2 may be removed from the wearer and washed or laundered. After the reusable diaper 2 (and fluid-absorbing insert 4) has been satisfactorily washed and dried, the reusable diaper 2 may be reused.

In other exemplary embodiments, reusable diapers may include fluid-absorbing inserts releasably coupled to the reusable diapers. For example, snaps, adhesives, buttons, clasps, various hook and loop closures, magnets, elastic straps, adjustable straps, combinations thereof, etc. may be used to couple the fluid-absorbing inserts to the reusable diapers. Here, when the fluid-absorbing inserts become saturated, soiled, etc., they may be washed and/or laundered either together with the reusable diaper or separate therefrom. If laundered separate, one the fluid-absorbing inserts and the reusable diapers are washed and dried, the fluid-absorbing inserts may be repositioned within and re-coupled to the reusable diapers for further use.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom," "side", "inner," "outer," etc. describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order or performance. It is also to be understood that additional or alternative steps may be employed.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A gender neutral reusable diaper, comprising:
   an inner layer comprising an absorbent material;
   an outer layer formed of a substantially liquid-impervious material;
   at least one fluid-absorbing insert for use in absorbing fluids;
   a forward waist portion defined by at least part of the inner layer; and
   a rearward waist portion defined by at least part of the inner layer;
   wherein the inner layer is disposed generally between the outer layer and the at least one fluid-absorbing insert;
   wherein the at least one fluid-absorbing insert has a first end and a second end opposite the first end, the first end is fastened to the inner layer at a first location adjacent the forward waist portion and the second end is fastened to the inner layer at a second location adjacent the rearward waist portion; and
   wherein the at least one fluid-absorbing insert includes a portion between the first and second ends that is adjustable relative to the inner layer between the first location and the second location for selectively changing an overlapped region of the at least one fluid-absorbing insert to accommodate use by a male and/or a female.

2. The gender neutral reusable diaper of claim 1, wherein the at least one fluid-absorbing insert includes at least two layers of material separate from each other along at least part of longitudinal edge portions of the at least two layers of material.

3. The gender neutral reusable diaper of claim 1, wherein the at least one fluid-absorbing insert is fastened to the inner layer by stitches adjacent the forward waist portion and adjacent the rearward waist portion.

4. The gender neutral reusable diaper of claim 1, further comprising a crotch portion disposed generally between the forward waist portion and the rearward waist portion.

5. The gender neutral reusable diaper of claim 4, further comprising an adjustment system adjacent the forward waist portion, the adjustment system allowing adjustment of the reusable diaper to fit different sized wearers.

6. The gender neutral reusable diaper of claim 5, wherein the adjustment system includes a three-by-three array of snaps along the outer layer of the reusable diaper, the array of snaps including at least a first row of at least three spaced-apart snaps vertically spaced from and aligned with corresponding snaps in at least two other rows of the array.

7. The gender neutral reusable diaper of claim 1, wherein the at least one fluid-absorbing insert is adjustable at a desired location between the forward waist portion and the rearward waist portion by folding at least part of the at least one fluid-absorbing insert over itself at the desired location.

8. The gender neutral reusable diaper of claim 7, wherein the at least one fluid-absorbing insert is adjustable for accommodating use by a male by folding at least part of the at least one fluid-absorbing insert over itself adjacent the forward waist portion.

9. The gender neutral reusable diaper of claim 7, wherein the at least one fluid-absorbing insert is adjustable for accommodating use by a female by folding at least part of the at least one fluid-absorbing insert over itself adjacent the crotch portion.

10. The gender neutral reusable diaper of claim 1, wherein the fluid-absorbing insert is at least partially formed from organic material.

11. The gender neutral reusable diaper of claim 1, wherein the inner layer includes at least one liquid-resistant region oriented for resisting wicking of moisture from the at least one fluid-absorbing insert along the inner layer past the at least one liquid-resistant region to a waist edge portion of the diaper.

12. The gender neutral reusable diaper of claim 11, wherein the inner layer includes at least two liquid-resistant regions, a first liquid-resistant region being located adjacent the forward waist portion and a second liquid-resistant region being located adjacent the rearward waist portion, the first liquid-resistant region oriented for resisting wicking of moisture from the at least one fluid-absorbing insert along the inner layer past the first liquid-resistant region to a forward waist edge portion of the diaper, and the second liquid-resistant region oriented for resisting wicking of moisture from the at least one fluid-absorbing insert along the inner layer past the second liquid-resistant region to a rearward waist edge portion of the diaper.

13. The gender neutral reusable diaper of claim 1, wherein the rearward waist portion has at least one resiliently stretchable corner region for use in securing the gender neutral reusable diaper in a desired position.

14. The gender neutral reusable diaper of claim 1, wherein the inner layer includes two or more layers and/or the outer layer includes two or more layers.

15. The gender neutral reusable diaper of claim 1, wherein the portion of the fluid-absorbing insert between the first and second ends is not directly attached to the inner layer.

16. A gender neutral reusable diaper, comprising:
a waist portion defining a waist edge portion of the diaper;
an outer layer formed of a substantially liquid-impervious material;
an inner layer comprising an absorbent material and defining at least part of the waist portion; and
at least one fluid-absorbing insert for use in absorbing fluids, a first end of the at least one fluid-absorbing insert fastened to the inner layer at a first location, a second end of the at least one fluid-absorbing insert opposite the first end fastened to the inner layer at a second location, the at least one fluid-absorbing insert being adjustable relative to the waist portion by folding a portion of the at least one fluid-absorbing insert between the first and second ends of the at least one fluid-absorbing insert over itself at a desired location between said first location and said second location to form an overlapped region of the at least one fluid-absorbing insert for accommodating use of the reusable diaper by a male and/or a female;
wherein the inner layer includes at least one liquid-resistant region disposed between the waist edge portion of the diaper and the at least one fluid-absorbing insert for resisting movement of fluid from the at least one fluid-absorbing insert along the waist portion to the waist edge portion of the diaper.

17. The gender neutral reusable diaper of claim 16, wherein the waist portion is a forward waist portion and the waist edge portion is a forward waist edge portion of the diaper, the gender neutral reusable diaper further comprising:
a rearward waist portion defining a rearward waist edge portion of the diaper; and
a crotch portion disposed generally between the forward waist portion and the rearward waist portion;
wherein the inner layer includes at least one liquid-resistant region disposed between the rearward waist edge portion of the diaper and the at least one fluid-absorbing insert for resisting movement of fluid from the at least one fluid-absorbing insert along the rearward waist portion to the rearward waist edge portion of the diaper.

18. The gender neutral reusable diaper of claim 16, wherein the at least one fluid-absorbing insert is stitched to the inner layer.

19. The gender neutral reusable diaper of claim 16, wherein the portion of the fluid-absorbing insert between the first and second ends is not directly attached to the inner layer.

20. A gender neutral reusable diaper, comprising:
an inner layer comprising an absorbent material;
an outer layer stitched to the inner layer, the outer layer formed of a substantially liquid-impervious material;
a forward waist portion defined by at least part of the inner layer;
a rearward waist portion opposite the forward waist portion and defined by at least part of the inner layer;
a crotch portion between the forward waist portion and the rearward waist portion and defined by at least part of the inner layer;
a fluid-absorbing insert having a first end, a second end opposite the first end, and a portion between the first and second ends;
wherein the forward waist portion, the rearward waist portion and the crotch portion cooperatively define leg openings to accommodate a wearer's legs when the gender neutral diaper is configured for use;
wherein the fluid-absorbing insert is attached to the inner layer opposite the outer layer, the first end of the fluid-absorbing layer is attached to the inner layer by stitching at a first location closer to the forward waist portion than the rearward waist portion, the second end of the fluid-absorbing layer is attached to the inner layer by stitching at a second location closer to the rearward waist portion than the forward waist portion; and
wherein the portion of the fluid-absorbing insert between the first and second ends is selectively overlappable to create an overlapped region of the fluid-absorbing insert at a selectable position between the first and second locations to accommodate use by a male when the overlapped region is positioned at a forward location adjacent the forward waist portion for absorbing fluids discharged by the male wearer or to accommodate use by a female when the overlapped region is positioned at a central location for absorbing fluids discharged by the female wearer.

21. The gender neutral reusable diaper of claim 20, wherein each of the forward waist portion and the rearward waist portion includes a liquid resistant region to resist movement of moisture from the crotch portion through the forward and rearward waist portions.

22. The gender neutral reusable diaper of claim 21, wherein the rearward waist portion has two resiliently stretchable corner regions releasably attachable to the forward waist portion for securing the gender neutral reusable diaper in a desired position.

23. The gender neutral reusable diaper of claim 22, further comprising an adjustment system on the outer layer of the gender neutral reusable diaper for adjusting a crotch length of the gender neutral reusable.

24. The gender neutral reusable diaper of claim 20, wherein the portion of the fluid-absorbing insert between the first and second ends is not directly attached to the inner layer.

* * * * *